United States Patent [19]

Cassidy et al.

[11] 4,299,970
[45] Nov. 10, 1981

[54] OXY-ALKYLAMINO CARBOXYLIC ESTERS

[75] Inventors: Frederick Cassidy; Gordon Wootton, both of Harlow, England

[73] Assignee: Beecham Group Limited, England

[21] Appl. No.: 181,432

[22] Filed: Aug. 25, 1980

Related U.S. Application Data

[60] Division of Ser. No. 739,033, Nov. 5, 1976, which is a continuation of Ser. No. 632,975, Nov. 18, 1975, abandoned.

[30] Foreign Application Priority Data

Nov. 29, 1974 [GB] United Kingdom ............... 51733/74

[51] Int. Cl.$^3$ .......................................... C07C 101/20
[52] U.S. Cl. .................... 560/39; 560/170; 424/309
[58] Field of Search ................... 260/404; 560/39, 170

[56] References Cited

U.S. PATENT DOCUMENTS

| | | | |
|---|---|---|---|
| 2,343,769 | 3/1940 | Gray | 260/404 |
| 2,582,257 | 1/1952 | Jones | 260/404 |
| 4,201,864 | 5/1980 | Cassidy et al. | 560/21 |

Primary Examiner—John F. Niebling
Attorney, Agent, or Firm—Jacobs & Jacobs

[57] ABSTRACT

Compounds of formula (I):

$$(CH_2)_m \diagdown_Z^{X \diagup CH_2-Y-(CH_2)_n-R_1} N \diagdown_{R_3}^{R_2} R_4 \quad (I)$$

wherein:
X is CO, protected CO, CROH in which R is hydrogen or $C_{1-4}$ alkyl and in which the OH moiety may be protected;
Y is $CH_2CH_2$ or $CH=CH$;
Z is CO or $CH_2$;
n is 1 to 8;
m is 1, 2 or 3;
$R_1$ is hydrogen, $CH_2OH$, $CH_2OH$ in which the OH moiety is protected, $CO_2W$ wherein W is hydrogen or $CO_2W$ represents an ester group in which the ester moiety contains from 1 to 12 carbon atoms, or $CONH_2$;
$R_2$ is hydrogen, $C_{1-4}$ alkyl, or taken together with $R_3$ and the carbon atom to which it is attached represents a carbonyl group;
$R_3$ is hydrogen, hydroxy or protected hydroxy;
$R_4$ is hydrogen or $C_{1-9}$ alkyl;
and salts thereof—have useful pharmacological properties.

8 Claims, No Drawings

OXY-ALKYLAMINO CARBOXYLIC ESTERS

CROSS-REFERENCE

This is a division of Ser. No. 739,033 filed Nov. 5, 1976 which in turn is a continuation of Ser. No. 632,975 filed Nov. 18, 1975, abandoned.

This invention relates to compounds having pharmaceutical activity, to a process for their production, to intermediates useful in that process and to pharmaceutical compositions containing the active compounds.

More specifically, this invention relates to cyclic amides and amines in which the nitrogen atom and one α-carbon atom are substituted by aliphatic groups, to the preparation of such compounds via novel carboxylic acids or their esters and to pharmaceutical compositions containing the cyclic amides and amines.

Natural prostaglandins and analogues thereof are known to possess a wide variety of pharmacological activities.

Offenlegungsschrift No. 2323193 discloses that pyrazolidine derivatives of the formula (I)':

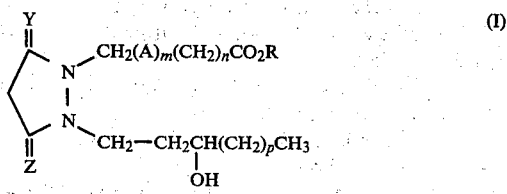

wherein A is CH=CH or C≡C; R is H, an alkali metal, an amine salt, or an ≥12C hydrocarbon or chlorohydrocarbon residue; m is 0 or 1; n is 0–6; p is 0–6; and Y and Z are O or $H_2$ except that Y and Z are not both O;

have similar biological properties to the prostaglandins or are antagonists of prostaglandins.

A paper by Bolliger and Muchowski (Tet. Letters, 1975, 2931) describes the preparation of 11-desoxy-8-azaprostaglandin $E_1$, but states only that one epimer thereof was more active in several biological assays than the other epimer.

A class of compounds has now been discovered within which useful pharmacological activity is displayed. For example compounds within this class have anti-gastric secretion activity, cardiovascular activity e.g. anti-hypertensive activity, platelet aggregation inhibition activity, effect the respiratory tract e.g. bronchodilator activity, and have antifertility and smooth muscle activity. In general it may be said that compounds within this class have a range of pharmacological activities similar to those shown by the natural prostaglandins, but that these activities tend to be rather more selective.

Accordingly the present invention provides a compound of the formula (I):

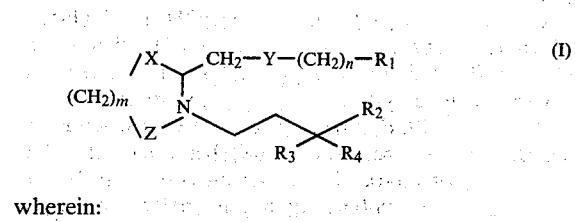

wherein:

X is CO, protected CO, CROH in which R is hydrogen or $C_{1-4}$ alkyl and in which the OH moiety may be protected;
Y is $CH_2CH_2$ or CH=CH;
Z is CO or $CH_2$;
n is 1 to 8;
m is 1, 2 or 3;
$R_1$ is hydrogen, $CH_2OH$, $CH_2OH$ in which the OH moiety is protected, $CO_2W$ wherein W is hydrogen or $CO_2W$ represents an ester group in which the ester moiety contains from 1 to 12 carbon atoms, or $CONH_2$.
$R_2$ is hydrogen, $C_{1-4}$ alkyl, or taken together with $R_3$ and the carbon atom to which it is attached represents a carbonyl group;
$R_3$ is hydrogen, hydroxy or protected hydroxy;
$R_4$ is hydrogen or $C_{1-9}$ alkyl;
and salts thereof.

In formula (I), often n will be 3 to 8, $R_2$ will be a hydrogen atom or methyl group, or taken together with $R_3$ and the carbon atom to which it is attached will represent a carbonyl group, and X will be CO, CROH in which R is hydrogen or $C_{1-4}$ alkyl and in which the OH moiety may be protected.

Suitable protected CO groups X include groups formed by conventional carbonyl addition and condensation reactions such as ketals, thioketals, hemithioketals, oximes, semicarbazones, hydrazones and the like. Of such groups often the ketal type derivatives will be most useful, for example when X is a group

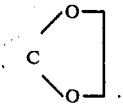

Examples of suitable groups X include CO, CHOH, $C(CH_3)OH$ and $C(C_2H_5)OH$. Preferably X is CO, CHOH or $C(CH_3)OH$, most preferably CO. Similarly it is often preferred that Y is $CH_2CH_2$ and also that Z is CO.

While n may be 1 to 8, n is most suitably 1 to 5. Within this narrower range, the preferred values for n include 3,4 and 5,3 being the most preferred. Thus it will be seen that the α side chain of the compounds of the formula (I) will often be of the formula $(CH_2)_{n'}R^1$ wherein $n^1$ is 6,7 or 8, preferably 6.

We believe that the most valuable compounds of the formula (I) are given when m is 1 and also when m is 2. Further, we have found that in some pharmacological test systems compounds wherein m is 1 demonstrate a rather higher potency than the corresponding compounds wherein m is 2.

Suitable protected hydroxy groups include readily hydrolysable groups such as acylated hydroxy groups in which the acyl moiety contains 1 to 4 carbon atoms, for example the acetoxy group, and hydroxy groups etherified by readily removable inert groups such as benzyl or like groups. Preferably the hydroxy moieties in formula (I) are unprotected.

Suitable groups $R_1$ include hydrogen, $CH_2OH$, $CO_2H$ and the methyl, ethyl, propyl, butyl, pentyl, hexyl, phenyl, benzyl, toluyl or like ester of the said $CO_2H$ acid group. Normally however $R_1$ will be hydrogen, $CH_2OH$, $CO_2H$ or a $C_{1-4}$ alkyl ester of the said $CO_2H$ acid group.

Of the variants possible for $R_2$, the most suitable include hydrogen, methyl and ethyl, and of these methyl and ethyl are often preferred. Most usually $R_2$ will be methyl.

$R_3$ is hydrogen, hydroxy or protected hydroxy. Suitable protected hydroxy groups $R_3$ have of course been described above. Preferably $R_3$ is hydrogen or hydroxy, most preferably hydroxy.

$R_4$ is hydrogen or a $C_{1-9}$ alkyl group. Suitable examples of $R_4$ include $C_{4-9}$ alkyl groups which may be straight chain alkyl groups, such as n-butyl, n-pentyl, n-hexyl and n-heptyl, or may be alkyl groups, such as the aforenamed alkyl groups, branched by one or two methyl groups (at the same or different carbon atoms).

Thus for example $R_4$ may be a group $CH_2R_5$, $CH(CH_3)R_5$ or $C(CH_3)_2R_5$, wherein $R_5$ is a straight chain alkyl group such that the carbon content of the resultant group $R_4$ is 4 to 9. Suitably $R_5$ is n-butyl or n-pentyl.

In general preferred groups $R_4$ include straight chain pentyl, hexyl and heptyl groups. Of these, straight chain hexyl is often the most useful.

The compounds of the formula (I) may form conventional acid salts when W is hydrogen. Such salts include those with alkali and alkaline earth metals, suitably sodium and potassium, and ammonium and substituted ammonium salts. Also, when Z is $CH_2$, the resultant amine of the formula (I) may form acid addition salts with conventional pharmaceutically acceptable acids. Examples of such acids include hydrochloric, hydrobromic, phosphone, acetic, fumaric, salicylic, citric, lactic, mandelic, tartaric and methylsulphonic acids.

A group of compounds of particular interest within formula (I) include compounds of the formula (II):

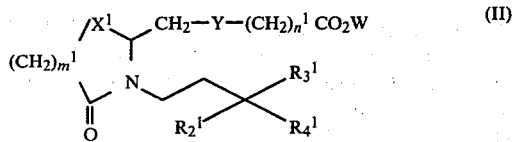

(II)

wherein:
$X^1$ is CO, or CHOH or $C(CH_3)OH$ in which the OH moieties may be protected;
$m^1$ is 1 or 2;
$n^1$ is 1 to 5;
$R^1_2$ is hydrogen or $C_{1-4}$ alkyl;
$R^1_3$ is hydrogen, hydroxy or protected hydroxy;
$R^1_4$ is hydrogen or $C_{4-9}$ alkyl; and
Y and W are as defined in formula (I); and salts thereof.

In formula (II), suitable examples of $X^1$ include CO, CHOH and $C(CH_3)OH$. Normally it is preferred that $X^1$ is CO, Y is $CH_2CH_2$, $m^1$ is 1, and $n^1$ is 3 or 5 (most preferably 3).

Suitably $R^1_2$ is hydrogen, methyl or ethyl. Of these three values, $R^1_2$ is most suitably methyl or ethyl, preferably methyl. Similarly, suitably $R^1_3$ is hydrogen or hydroxy, preferably hydroxy.

Suitable and preferred straight chain and branched alkyl groups $R^1_4$ include those previously described as suitable and preferred for the group $R_4$ when $R_4$ is a $C_{4-9}$ alkyl group. Such preferred groups $R^1_4$ include straight chain pentyl, hexyl and heptyl, and of these normally the most useful is straight chain hexyl.

Of the variants possible for W as defined in formula (I), normally we prefer that W is hydrogen or a $C_{1-4}$ alkyl group such as the methyl or ethyl groups.

Thus it can be seen that within formula (II) there is a sub-group of particular utility of the formula (III):

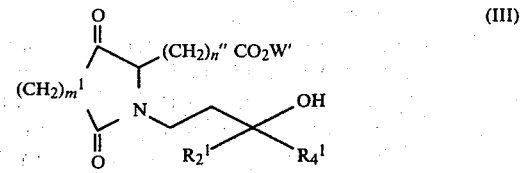

(III)

wherein:
$m^1$ is 1 or 2;
$n^{11}$ is 6 or 8;
$R^1_2$ is hydrogen, methyl or ethyl;
$R^1_4$ is n-pentyl, n-hexyl or n-heptyl; and
$W$ is hydrogen or $C_{1-4}$ alkyl; and salts thereof.

In formula (III), $m^1$ is preferably 1 and $n^{11}$ is preferably 6. Similarly $R^1_2$ is most usefully methyl or ethyl (preferably methyl), and $R^1_4$ is preferably n-hexyl. Lastly in formula (III) $W^1$ is most suitably a $C_{1-4}$ alkyl group such as the methyl or ethyl group.

The most useful compounds within formula (III) include the following:
2-(6'-Ethoxycarbonyl-n-hexyl)-1-(3''-hydroxy-3''-methyl-n-nonyl)-pyrrolidin-3,5-dione.
2-(6'-Ethoxycarbonyl-n-hexyl)-1-(3''-hydroxy-3''-methyl-n-octyl)-pyrrolidin-3,5-dione.
2-(6'-Ethoxycarbonyl-n-hexyl)-1-(3''-hydroxy-3''-methyl-n-decyl)-pyrrolidin-3,5-dione.
2-(6'-Ethoxycarbonyl-n-hexyl)-1-(3''-hydroxy-3''-ethyl-n-nonyl)-pyrrolidin-3,5-dione.

In formula (I), when Z is $CH_2$ a useful group of compounds includes those of formula (IV):

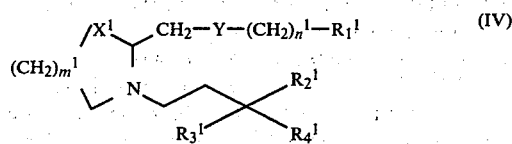

(IV)

wherein: $X^1$, Y, $m^1$, $n^1$, $R^1_2$, $R^1_3$ and $R^1_4$ are as defined in formula (II); and $R^1_1$ is $CH_3$, $CH_2OH$ or $CH_2OH$ in which the OH moiety is protected; and salts thereof.

$X^1$ in formula (IV) may be CO, CHOH or $C(CH_3)OH$ in which the OH moiety may be protected. In general it may be said that $X^1$ is most usefully CHOH or $C(CH_3)OH$. Also Y is preferably $CH_2CH_2$, and $n^1$ is preferably 3 or 5 (most preferably 3).

Suitable examples of the group $R^1_2$ include hydrogen, methyl and ethyl, preferred examples include hydrogen and methyl. In the same way, suitable examples of $R^1_3$ include hydrogen and hydroxy.

Suitable and preferred examples of the group $R^1_4$ include those described for $R^1_4$ in relation to formula (II).

$R^1_1$ may be $CH_3$, $CH_2OH$ or $CH_2OH$ in which the OH moiety is protected. When $R^1_1$ is $CH_3$, then often $R^1_2$ and $R^1_3$ will be hydrogen, $R^1_4$ will represent a straight chain pentyl, hexyl or heptyl group, and $X^1$ will be CHOH or $C(CH_3)OH$. In the same way when $R_1$ is $CH_2OH$ (or less preferably $CH_2OH$ in which the OH moiety is protected), $X^1$ will normally be CHOH or $C(CH_3)OH$, $R^1_2$ will be hydrogen, methyl or ethyl, preferably hydrogen or methyl, and $R^1_3$ will be hydrogen or hydroxy.

A second useful group of compounds when Z is $CH_2$ are those of formula (V):

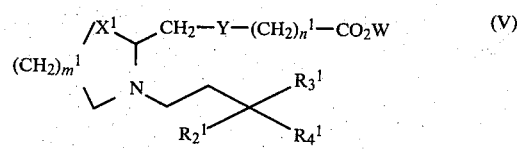

wherein: $m^1$, $n^1$, $X^1$, Y, W, $R^1_2$, $R^1_3$ and $R^1_4$ are as defined in formula (II); and salts thereof.

In formula (V) it is normally preferred that $n^1$ is 3 or 5, most preferably 3, and that Y is $CH_2CH_2$.

Suitably $X^1$ is CO, CHOH or $C(CH_3)OH$, while of these values $X^1$ is most often CO.

$R^1_2$ is hydrogen or $C_{1-4}$ alkyl, and suitable examples of such groups $R^1_2$ include hydrogen, methyl and ethyl, preferably methyl. Again, suitably $R^1_3$ in formula (V) is hydrogen or hydroxy, preferably hydroxy.

Suitable and preferred values for $R^1_4$ and W in formula (V) include those values stated to be suitable and preferred for $R^1_4$ and W earlier in the specification in relation to formula (II).

It will of course be realised that the compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the usual methods.

The present invention also provides a process for the preparation of a compound of the formula (I), which process comprises either decarboxylating a compound of the formula (VI):

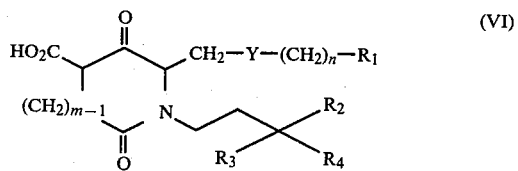

wherein m, n, Y, $R_1$, $R_2$, $R_3$ and $R_4$ are as defined in formula (I), to yield a compound of the formula (I) wherein X is CO, and thereafter if desired converting X in the thus formed compound to protected CO by conventional methods, or to CROH by reduction when R is hydrogen or by reaction with a $C_{1-4}$ alkyl Grignard reagent or $C_{1-4}$ alkyl metallic complex when R is $C_{1-4}$ alkyl, and then optionally protecting the CROH hydroxy moiety; or reacting a compound of the formula (I) wherein Z is CO with a vigorous reducing agent to convert it into the coresponding compound wherein Z is $CH_2$ and wherein other carbonyl functions present in the chosen compound of the formula (I) are reduced, and thereafter if desired oxidising one or more of these reduced carbonyl functions back to carbonyl functions.

The decarboxylation reaction may be brought about under basic, acid or neutral conditions in conventional manner. For example when m=1 the reaction is conveniently effected by heating the chosen compound of the formula (VI) in a suitable solvent such as toluene or xylene.

The conversion of a compound of the formula (I) wherein X is CO to the corresponding compound wherein X is protected CO may be carried out under conventional reaction conditions for, for example, carbonyl addition and condensation reactions.

The conversion of a compound of the formula (I) wherein X is CO to the corresponding compound where X is CHOH may be carried out by conventional methods for reducing a ketone to an alcohol, for example by sodium borohydride reduction.

The conversion of a compound of the formula (I) wherein X is CO to the corresponding compound wherein X is CROH in which R is $C_{1-4}$ alkyl may be carried out by conventional Grignard or alkyl metal, (suitably alkyl lithium) reactions.

After the decarboxylation reaction the group W may be varied in compounds wherein $R_1$ is $CO_2W$ by conventional de-esterification and/or esterification reactions. Similarly protected CROH and $R_3$ hydroxy moieties may be deprotected by conventional methods. For example, when $R_3$ is a benzyloxy group, the benzyl group may readily be removed by hydrogenolysis. Thus it may be seen that 'protected hydroxy' compounds of the formula (I) are useful intermediates in the preparation of the corresponding 'free hydroxy' compounds of the formula (I).

When W is hydrogen, salts of compounds of the formula (I) may be prepared in conventional manner, for example by reacting the chosen compound of the formula (I) with the required base.

Similarly compounds of the formula (I) wherein $R_1$ is $CONH_2$ may be prepared by conventional methods from other compounds of the formula (I), for example by ammonolysis of the corresponding compound wherein $R_1$ is an ester group $CO_2W$.

Also compounds of the formula (I) wherein $R_3$ is OH may be prepared by conventional reduction or Grignard reactions on the corresponding compound wherein $CR_2R_3$ is a carbonyl group.

The reduction of a compound of the formula (I) wherein Z is CO to give the corresponding compound wherein Z is $CH_2$ requires a vigorous reducing agent. Suitable such reagents include lithium aluminium hydride and its chemical equivalents. The reaction conditions used for this reaction are generally those conventionally associated with the use of lithium aluminium hydride.

Due to the potency of the reducing agent used to effect the desired Z=CO to Z=$CH_2$ conversion in a compound of the formula (I), if the starting compound of the formula (I) wherein Z=CO contains a carbonyl function in addition to that of Z, then this additional carbonyl function will also be reduced. Accordingly when compounds of the formula (I) wherein Z is $CH_2$ are required in which such other carbonyl functions are present, they must be prepared from corresponding compounds of the formula (I) wherein Z is the $CH_2$ and the said other carbonyl functions are reduced, by selective oxidation. Examples of such selective oxidation are given in the following three paragraphs.

A compound of the formula (I) wherein Z is $CH_2$ and X is CO may be prepared by the oxidation of the corresponding compound wherein X is CHOH. A suitable oxidising agent for this reaction is a chromium trioxide-pyridine mixture in methylene chloride.

A compound of the formula (I) wherein Z is $CH_2$ and $R_1$ is a group $CO_2W$ may be prepared by the oxidation and optional subsequent salification or esterification of the corresponding compound of the formula (I)

wherein $R_1$ is $CH_2OH$. A suitable oxidising agent for this reaction is a chromic acid-acetic acid mixture.

A compound of the formula (I) wherein Z is $CH_2$ and $CR_2R_3$ represents a carbonyl group may be prepared by the oxidation of the corresponding compound of the formula (I) wherein $CR_2R_3$ is a CHOH group. A suitable oxidising agent for this reaction is a chromium trioxide-pyridine mixture in methylene chloride.

It will be realised that the optional interconversions described above for compounds of the formula (I) wherein Z is CO after their preparation by decarboxylation may just as readily be carried out with compounds of the formula (I) wherein Z is $CH_2$ after their preparation by reduction.

It is frequently convenient to generate the compound of formula (VI) in situ from a corresponding ester of the formula (VII):

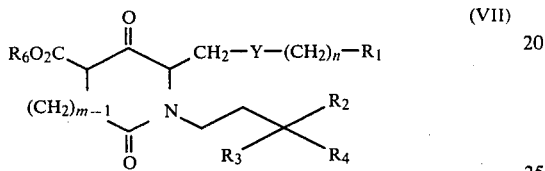

where $CO_2R_6$ is a conventional ester group. In such a case $R_6$ is preferably a benzyl group or a lower alkyl group such as methyl or ethyl or the like. It has been found that often it is sufficient to bring about de-esterification and subsequent decarboxylation in the chosen compound of the formula (VII) simply to leave the compound standing in an inert solvent, for example overnight. Otherwise the desired de-esterification and decarboxylation in the chosen compound of the formula (VII) can be brought about by treatment with, for example, lithium iodide dihydrate and collidine in anhydrous solvents. In cases where $m=1$, the compound of the formula (VII) can also for example be de-esterified and decarboxylated by heating the compound alone or preferably, in a high boiling solvent such as toluene or xylene.

It will be appreciated that compounds of the formulae (VI) and (VII) are useful intermediates and as such form a useful aspect of this invention.

The compounds of formula (VII) may be prepared by the ring closure of the corresponding diester of formula (VIII):

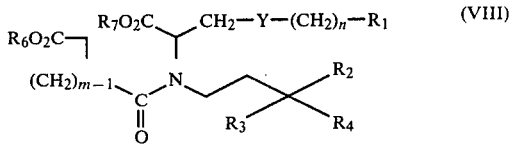

wherein m, n, Y, $R_1$, $R_2$, $R_3$ and $R_4$ are as defined in formula (I), $R_6$ is as defined in formula (VII), and $R_7$ is a group such that $CO_2R_7$ is an ester group.

In the processes of the invention the group $R_1$ in the intermediates of formula (VI), (VII) and (VIII) will often represent an ester group $CO_2W$, and if for example acids of the formula (I) (wherein $R_1$ is $CO_2H$) are required they can be obtained by de-esterification of the corresponding compound of the formula (I) wherein $R_1$ is an ester group $CO_2W$. Usually the ester group $CO_2R_7$ in formula (VIII) will be the same ester group as $CO_2W$, and for the sake of convenience the ester group $CO_2R_6$ will also normally be the same ester group as $CO_2W$. The ester groups $CO_2W/R_6/R_7$ are suitably $C_{1-4}$ alkyl esters such as methyl and ethyl esters.

Generally, the ring closure takes place in a dry organic solvent using a strong base such as sodium hydride or sodium ethoxide (or other $-OR_6$ or $-OR_7$ group) to bring about the initial proton abstraction from the α-methylene group. It has been found that sodium ethoxide in benzene, or potassium t-butoxide in toluene, benzene or hexamethylphosphoramide give good results.

Compounds of formula (VIII) are novel useful intermediates and as such, form an aspect of this invention.

Compounds of formula (VIII) may be prepared by the esterification of a corresponding acid or by the reaction of a compound of the formula (IX):

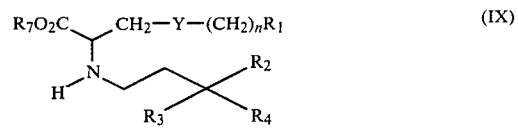

with a reactive acylating derivative of an acid of the formula (X):

$$HO_2C-(CH_2)_m-CO_2H \quad (X)$$

or an ester thereof.

Suitable reactive acylating derivatives include (a) compounds of the formula (XI):

$$R_6O_2C-(CH_2)_m-CO-Z \quad (XI)$$

where Z is a readily displaceable group such as Cl, Br, $OSO_2CH_3$, $OSO_2C_6H_4CH_3$, $OCO(CH_2)_mCO_2R_6$ or the like, (b) compounds of the formula (XI) wherein Z is OH in the presence of dicyclohexyl carbodiimide as a condensing agent, and (c) cyclic anhydrides such as:

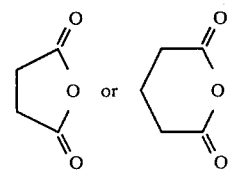

The reaction of the compound (IX) with the compound (X) or (XI) occurs under conventional acylation conditions.

The novel substituted amino acids (IX) are highly useful intermediates and form an important aspect of the present invention.

The compounds (IX) may be prepared by the reaction of an amine of the formula (XII):

$$H_2N-CH_2CH_2CR_2R_3R_4 \quad (XII)$$

with a compound of the formula (XIII):

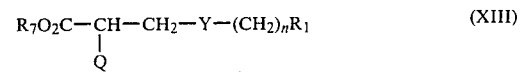

where Q is a group readily displaceable by an electron rich group.

Suitable groups Q include I, Br, Cl, $O.SO_2.CH_3$, $O.SO_2C_6H_4CH_3$ and other conventional groups.

The displacement reaction occurs under conventional reaction conditions, for example, in an alcoholic solvent in the presence of $Na_2CO_3$ or pyridine.

Compounds within the formula (I) have useful pharmacological activity. For example compounds within the formula (I) have anti-gastric secretion activity, cardiovascular activity e.g. anti-hypertensive activity, platelet aggregation inhibition activity, effect the respiratory tract e.g. bronchodilator activity, and have anti-fertility and smooth muscle activity.

In general it may be said that compounds within the formula (I) have a range of pharmacological activities similar to those shown by the natural prostaglandins, but that these activities tend to be rather more selective.

The invention therefore also provides a pharmaceutical composition comprising a compound of the formula (I) and a pharmaceutically acceptable carrier.

Clearly the formulation of the said pharmaceutical composition will depend on the nature of the activity shown by the chosen compound of the formula (I), and on other factors such as a preference in a particular area of therapy for a particular mode of administration. In general however the compositions may be formulated for administration by any route.

The compositions may be in the form of tablets, capsules, powders, granules, lozenges or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; filler for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents. The compounds of the formula (I) may also if desired be incorporated in a foodstuff, for example in the form of a biscuit.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for, or as a microfine powder for insufflation.

As is common practice, the compositions will usually be accompanied by written or printed directions for use in the medical treatment concerned.

It has been found that a number of the compounds of the formula (I) are potent inhibitors of gastric secretion, and thus have commercial utility as anti-ulcer agents. In treatment of this nature, the composition containing the formula (I) will preferably be formulated in a manner to allow oral administration. Normally 0.01 mg/kg to 500 mg/kg per day, most suitably 0.1 to 100 mg/kg per day, of the compound of the formula (I) in composition form will be administered in such treatment. Examples of such compounds of the formula (I) include those of formulae (II) and (III) as hereinbefore defined.

Also a number of compounds of the formula (I) have particularly useful activity on the respiratory tract, and thus find utility as for example bronchodilators. Normally compositions containing such compounds of the formula (I) will be formulated as an aerosol, or as a microfine powder for insufflation, and the treatment will comprise the administration of from 0.001 mg/kg to 100 mg/kg per day of the compound in composition form.

Further, a number of compounds of the formula (I) are particularly potent inhibitors of platelet aggregation, and thus compositions containing such compounds are useful inter alia for administration to humans and animals to prevent clot formation for example after surgery to prevent postoperative thrombosis; in geriatric patients to prevent transient cerebral ischemic attacks; and long-term prophylaxis following myocardial infarcts and strokes—and in general in the treatment or prophylaxis of any disorder caused by an over pronounced tendency of blood platelets to aggregate. Such compositions also have applications in the storage of whole blood in blood banks, and whole blood to be used in heart-lung machines, or to be circulated through organs, e.g heart and kidneys, which have been removed from a cadaver and prior to transplant.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or propylaxis of disorders in human beings which comprises the administration to the sufferer of an effective amount of a compound of the formula (I).

It will be realised that when the compound of the formula (I) exhibits platelet aggregration inhibition activity then the invention also provides a method of inhibiting such aggregration in vivo.

The following Examples illustrate the preparation of compounds of the formula (I) and their pharmacological properties.

EXAMPLE 1

(PhCH$_2$)$_2$NCH$_2$CH$_2$COR

N,N,-Dibenzyl-2-aminoethyl methyl ketone (R=CH$_3$)

Freshly distilled methyl vinyl ketone (70.5 g) was added dropwise with stirring to a solution of dibenzylamine (197 g) in dry ethanol (50 ml) and the mixture was stirred for 30 minutes.

The solvent was evaporated and the solid residue washed with a small amount of ethanol to give N,N-dibenzyl-2-aminoethyl methyl ketone as a pale yellow solid (211.6 g, 79% yield), m.p. 58°–59°.

N,N-Dibenzyl-2-aminoethyl ethyl ketone (R=C$_2$H$_5$)

N,N-Dibenzyl-2-aminoethyl ethyl ketone was similarly obtained as a yellow oil from ethyl vinyl ketone and dibenzylamine.

EXAMPLE 2

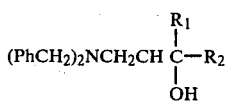

3-Methyl-1-(N,N-dibenzylamino)-nonan-3-ol (R$_1$=CH$_3$; R$_2$=C$_6$H$_{13}$)

Hexyl magnesium bromide was prepared under nitrogen from magnesium (6.55 g) and hexyl bromide (48.9 g) in dry tetrahydrofuran (100 ml).

A solution of N,N-dibenzyl-2-aminoethyl methyl ketone (50 g) in dry tetrahydrofuran (200 ml) was added dropwise to the Grignard reagent. The mixture was stirred and refluxed overnight.

A saturated solution of ammonium chloride was added and the product extracted three times with ether. The organic fractions were combined, dried over magnesium sulphate and evaporated to give 3-methyl-1-(N,N-dibenzylamino)-nonan-3-ol as a yellow oil (68.6 g).

The products shown in Table 1 were similarly prepared:

TABLE 1

| Grignard Reagent | Product R$_1$ | R$_2$ |
|---|---|---|
| C$_4$H$_9$MgBr | CH$_3$ | C$_4$H$_9$ |
| C$_5$H$_{11}$MgBr | CH$_3$ | C$_5$H$_{11}$ |
| C$_7$H$_{15}$MgBr | CH$_3$ | C$_7$H$_{15}$ |
| C$_8$H$_{17}$MgBr | CH$_3$ | C$_8$H$_{17}$ |
| C$_5$H$_{11}$CH(CH$_3$)MgBr | CH$_3$ | C$_5$H$_{11}$CH(CH$_3$) |
| C$_6$H$_{13}$MgBr | C$_2$H$_5$ | C$_6$H$_{13}$ |

EXAMPLE 3

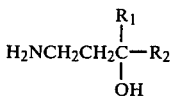

1-Amino-3-methyl-nonan-3-ol (R$_1$=CH$_3$; R$_2$=C$_6$H$_{13}$)

A solution of 3-methyl-1-(N,N-dibenzylamino)-nonan-3-ol (71 g) in ethanol (200 ml) was added to a slurry of 10% Pd/C (8 g) in ethanol. The mixture was hydrogenated at 70° and 200 psi for 3 days. The mixture was filtered through kieselguhr and evaporated. The oily product was fractionally distilled to give 1-amino-3-methyl-nonan-3-ol as a colourless liquid (18.9 g, 55% yield), b.p. 104°–106°/0.2 mm Hg.

The products shown in Table 2 were similarly prepared:

TABLE 2

| COMPOUND | R$_1$ | R$_2$ | Bp |
|---|---|---|---|
| 1$^{(a)}$ | CH$_3$ | C$_4$H$_9$ | 70–82°/0.1mm |
| 2 | CH$_3$ | C$_5$H$_{11}$ | 114–118°/1.5 mm |
| 3 | CH$_3$ | C$_7$H$_{15}$ | 104°/0.8mm |
| 4 | CH$_3$ | C$_8$H$_{17}$ | — |
| 5 | CH$_3$ | CH(CH$_3$)C$_5$H$_{11}$ | — |
| 6 | C$_2$H$_5$ | C$_6$H$_{13}$ | 100°/0.2mm |

$^{(a)}$few drops of acid added to facilitate hydrogenolysis

EXAMPLE 4

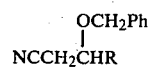

3-Benzyloxy-n-nonanitrile (R=C$_6$H$_{13}$)

1-Cyano-non-2-ene (311 g) was added dropwise to a stirred solution of sodium (6.5 g) in benzyl alcohol (722 g) at room temperature. The mixture was stirred and heated on a water bath for 4 hours and was then allowed to stand at room temperature overnight.

The reaction mixture was carefully neutralised with glacial acetic acid and the excess benzyl alcohol was evaporated in vacuo. The residue was taken up in ether, filtered and the filtrate evaporated in vacuo. The product was distilled to give 3-benzyloxy-n-nonanitrile as a colourless pungent oil (302 g, 54% yield), b.p. 166°–168°/0.6 mm Hg.

3-Benzyloxy-n-octanitrile (R=C$_5$H$_{11}$) was similarly prepared as a colourless oil, b.p. 128°–130°/0.25 mm Hg.

EXAMPLE 5

3-Benzyloxy-n-octylamine (R=C$_5$H$_{11}$)

3-Benzyloxy-n-octanitrile (74 g) was added dropwise to a stirred suspension of lithium aluminium hydride (12.2 g) in dry ether (450 ml). The reaction mixture was refluxed for 40 minutes and then cooled in an ice-bath.

Water was added dropwise to destroy the excess hydride. The solution was filtered and the solid residue washed several times with ether. The combined ether solutions were dried over magnesium sulphate and evaporated in vacuo. The product was distilled to give 3-benzyloxy-n-octylamine as a colourless oil (70.4 g, 94% yield), b.p. 129°/0.4 mm Hg.

3-Benzyloxy-n-nonylamine (R=C$_6$H$_{13}$) was similarly prepared as a colourless oil, b.p. 136°–140°/0.1 mm Hg.

EXAMPLE 6

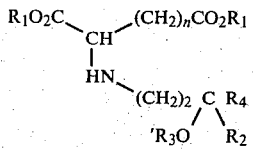

Diethyl 2-(N-3'-benzyloxy-n-nonyl)-aminoazelate
(n=6; $R_1$=$C_2H_5$; $R_2$=H; '$R_3$=$CH_2Ph$; $R_4$=$C_6H_{13}$)

A solution of diethyl 2-bromoazelate (114 g) in dry ethanol (200 ml) was added dropwise to a refluxing solution of 3-benzyloxy-n-nonylamine (80 g) in dry ethanol (500 ml) containing a suspension of anhydrous sodium carbonate (41 g). The mixture was refluxed with stirring for 12 hours.

The reaction mixture was filtered and the filtrate evaporated in vacuo. The residue was taken up in ether (500 ml) and the ethereal solution was washed with saturated brine until neutral, dried over magnesium sulphate and evaporated in vacuo to give diethyl 2-(N-3'-benzyloxy-n-nonyl)-aminoazelate as a yellow oil (164 g).

The products shown in Table 3 were similarly prepared:

TABLE 3

| COMPOUND | n | $R_1$ | $R_2$ | $R_3$ | $R_4$ |
|---|---|---|---|---|---|
| 7 | 6 | $C_2H_5$ | H | $CH_2Ph$ | $C_5H_{11}$ |
| 8 | 6 | $C_2H_5$ | H | $CH_2Ph$ | H |
| 9 | 6 | $C_2H_5$ | $CH_3$ | H | $C_4H_9$ |
| 10 | 6 | $C_2H_5$ | $CH_3$ | H | $C_5H_{11}$ |
| 11 | 6 | $C_2H_5$ | $CH_3$ | H | $C_6H_{13}$ |
| 12 | 6 | $C_2H_5$ | $CH_3$ | H | $C_7H_{15}$ |
| 13 | 6 | $C_2H_5$ | $CH_3$ | H | $C_8H_{17}$ |
| 14 | 6 | $C_2H_5$ | $C_2H_5$ | H | $C_6H_{13}$ |
| 15 | 6 | $CH_3$ | $CH_3$ | H | $C_6H_{13}$ |
| 16 | 5 | $C_2H_5$ | $CH_3$ | H | $C_6H_{13}$ |
| 17 | 7 | $C_2H_5$ | $CH_3$ | H | $C_6H_{13}$ |
| 18 | 6 | $C_2H_5$ | $CH_3$ | H | $CH(CH_3)C_5H_{11}$ |

Ethyl 2-(N-n-octyl)-aminononanoate was similarly prepared as a colourless liquid from ethyl 2-bromononanoate and octylamine.

EXAMPLE 7

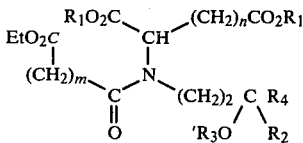

Method Variant A

Diethyl 2-[N-(3'-benzyloxy-n-octyl)-N-(3''-ethoxycarbonylpropionyl)]-aminoazelate (m=2; n=6; $R_1$=$C_2H_5$; $R_2$=H; '$R_3$=$CH_2Ph$; $R_4$=$C_5H_{11}$)

Diethyl 2-(N-3'-benzyloxy-n-octyl)-aminoazelate (18 g) was refluxed with succinic anhydride (3.9 g) in dry benzene (100 ml) overnight. The benzene was evaporated in vacuo and the residue was dissolved in ether. The ether solution was extracted with 10% sodium hydroxide solution. The aqueous phase was washed with ether, cooled to 0° and carefully acidified with concentrated hydrochloric acid. An oil separated and was extracted into ether. This ether solution was washed with water, dried over magnesium sulphate and evaporated in vacuo to give a yellow gum.

The product was refluxed for 2 hours with a 3% solution of acetyl chloride in dry ethanol (200 ml). The solution was concentrated and poured into water (200 ml). The product was extracted into ether and the ethereal solution was washed with with water, dried over magnesium sulphate and evaporated to give diethyl 2-[N-(3'-benzyloxy-n-octyl)-N-(3''-ethoxycarbonylpropionyl)]-aminoazelate as a yellow gum (17.3 g).

Method Variant B

Diethyl 2-[N-(3'-benzyloxy-n-octyl)-N-ethoxycarbonylacetyl]-aminoazelate (m=1; n=6; $R_1$=$C_2H_5$; $R_2$=H; '$R_3$=$CH_2Ph$; $R_4$=$C_5H_{11}$).

Ethyl chloroformylacetate (4 g) in dry benzene (10 ml) was added dropwise to a refluxing solution of diethyl 2-(N-3'-benzyloxy-n-octyl)-aminoazelate (8.3 g) in dry benzene (30 ml) and the mixture was refluxed for 4 hours. The benzene was evaporated in vacuo and the residue was taken up in ether.

The ether solution was washed with 5% sodium bicarbonate solution and with water, dried over magnesium sulphate and evaporated in vacuo to give a yellow oil. The product was purified by column chromatography to give diethyl 2-[N-(3'-benzyloxy-n-octyl)-N-(ethoxycarbonylacetyl)]-aminoazelate (3.9 g, 38% yield) as a yellow gum.

Method Variant C

Diethyl 2-[N-(3'-hydroxy-3'-methyl-n-nonyl)-N-ethoxycarbonylacetyl]-aminoazelate (m=1; n=6; $R_1$=$C_2H_5$; $R_2$=$CH_3$; '$R_3$=H; $R_4$=$C_6H_{13}$)

A solution of monoethyl malonate (6.85 g) in dry methylene chloride (100 ml) was added to a solution of diethyl 2-[N-(3'-hydroxy-3'-methyl-n-nonyl)]-aminoazelate (22.9 g) in dry methylene chloride (100 ml). The mixture was stirred at room temperature and a solution of dicyclohexylcarbodiimide (11.8 g) in dry methylene chloride (25 ml) was added dropwise. Stirring was continued overnight.

The mixture was filtered and the filtrate evaporated in vacuo. The residue was taken up in ether and the ethereal solution was washed with dilute hydrochloric acid, sodium bicarbonate solution and then with sodium chloride solution until the washings were neutral. The ether layer was dried over magnesium sulphate and evaporated in vacuo to give diethyl 2-[N-(3'-hydroxy-3'-methyl-n-nonyl)-N-ethoxy-carbonylacetyl]-aminoazelate as a yellow oil (27.5 g).

Method Variant D

Diethyl 2-[N-(3'-hydroxy-3'-methyl-n-decyl)-N-(3''-ethoxycarbonylpropionyl)]-aminoazelate (m=2; n=6; $R_1$=$C_2H_5$; $R_2$=$CH_3$; '$R_3$=H; $R_4$=$C_7H_{15}$).

A solution of monoethyl succinate (10.2 g) in dry methylene chloride (30 ml) was added to a solution of diethyl 2-[N-(3'-hydroxy-3'-methyl-n-decyl)]-aminoazelate (30 g) in dry methylene chloride (100 ml). The mixture was stirred at room temperature and a solution of dicyclohexylcarbodiimide (15.8 g) in dry methylene chloride (50 ml) was added dropwise. Stirring was continued overnight.

The mixture was filtered and the filtrate evaporated in vacuo. The residue was taken up in ether and the ethereal solution was washed with dilute hydrochloric acid, sodium bicarbonate solution and then with sodium chloride until the washings were neutral. The ether layer was dried over magnesium sulphate and evaporated in vacuo to give diethyl 2-[N-(3'-hydroxy-3'-methyl-n-decyl)-N-(3''-ethoxycarbonyl-propionyl)]-aminoazelate as a yellow oil (41.8 g).

The products shown below in Table 4 were similarly prepared.

TABLE 4

| COMPOUND | m | n | $R_1$ | $R_2$ | $'R_3$ | $R_4$ | Method Variant |
|---|---|---|---|---|---|---|---|
| 19 | 2 | 6 | $C_2H_5$ | H | $CH_2Ph$ | $C_6H_{13}$ | A |
| 20 | 1 | 6 | $C_2H_5$ | H | $CH_2Ph$ | $C_6H_{13}$ | B |
| 21 | 1 | 6 | $C_2H_5$ | H | $CH_2Ph$ | H | B |
| 22 | 2 | 6 | $C_2H_5$ | $CH_3$ | H | $C_8H_{17}$ | D |
| 23 | 2 | 7 | $C_2H_5$ | $CH_3$ | H | $C_6H_{13}$ | D |
| 24 | 2 | 6 | $C_2H_5$ | $CH_3$ | H | $CH(CH_3)C_5H_{11}$ | D |
| 25 | 2 | 6 | $C_2H_5$ | $CH_3$ | H | $C_6H_{13}$ | D |
| 26 | 2 | 6 | $C_2H_5$ | $CH_3$ | H | $C_5H_{11}$ | D |
| 27 | 1 | 6 | $C_2H_5$ | $CH_3$ | H | $C_4H_9$ | C |
| 28 | 1 | 6 | $C_2H_5$ | $CH_3$ | H | $C_5H_{11}$ | C |
| 29 | 1 | 6 | $C_2H_5$ | $CH_3$ | H | $C_7H_{15}$ | C |
| 30 | 1 | 6 | $C_2H_5$ | $CH_3$ | H | $C_8H_{17}$ | C |
| 31 | 1 | 7 | $C_2H_5$ | $CH_3$ | H | $C_6H_{13}$ | C |
| 32 | 1 | 5 | $C_2H_5$ | $CH_3$ | H | $C_6H_{13}$ | C |
| 33 | 1 | 6 | $C_2H_5$ | $C_2H_5$ | H | $C_6H_{13}$ | C |
| 34 | 1 | 6 | $CH_3$ | $CH_3$ | H | $C_6H_{13}$ | C |

Ethyl 2-[N-(3'-ethoxycarbonylpropionyl)-N-n-octyl]-aminononanoate was similarly prepared as a colourless oil, b.p. 222°/1 mm Hg using Method Variant A.

EXAMPLE 8

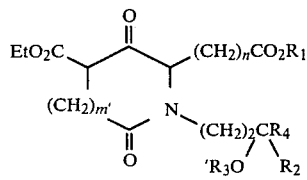

Method Variant A

4-Ethoxycarbonyl-2-(6'-ethoxycarbonyl-n-hexyl)-1-(3''-hydroxy-3''-methyl-n-nonyl)-pyrrolidin-3,5-dione (m'=0; n=6; $R_1=C_2H_5$; $R_2=CH_3$; $^1R_{3;I}=H$; $R_4=C_6H_{13}$)

Potassium tert-butoxide (5.35 g) was added in small portions over 1 hour to a warm solution of diethyl 2-[N-(3'-hydroxy-3'-methyl-n-nonyl)-N-ethoxycarbonylacetyl]-aminoazelate (27.5 g) in dry toluene (150 ml). The mixture was gently refluxed for 2 hours.

The solvent was evaporated in vacuo and the residue was taken up in water. The solution was extracted twice with ether and the aqueous layer was acidified with dilute hydrochloric acid and extracted with ether. This ethereal solution was washed with brine and dried over magnesium sulphate to give a solution of 4-ethoxycarbonyl-2-(6'-ethoxycarbonyl-n-hexyl)-1-(3''-hydroxy-3''-methyl-n-nonyl)-pyrrolidin-3,5-dione.

Method Variant B 1-(3'-Benzyloxy-n-octyl)-4-ethoxycarbonyl-2-(6''-ethoxycarbonyl-n-hexyl)-piperidin-3,5-dione (m'=1; n=6; $R_1=C_2H_5$; $R_2=H$; $^1R_3=CH_2Ph$; $R_4=C_5H_{11}$)

Diethyl 2-[N-(3'-benzyloxy-n-octyl)-N-(3''-ethoxycarbonylpropionyl)]-aminoazelate (5 g) was refluxed with potassium tert-butoxide (1.05 g) in dry benzene (50 ml) for 4 hours. The benzene was evaporated in vacuo and the residue poured into water (100 ml). The aqueous mixture was made just acidic with dilute hydrochloric acid and was extracted with ether. The ethereal solution was washed with water, dried over magnesium sulphate and evaporated in vacuo to give 1-(3'-benzyloxy-n-octyl)-4-ethoxycarbonyl-2-(6''-ethoxycarbonyl-n-hexyl)-piperidin-3,6-dione as a yellow gum, (4.5 g).

Method Variant C

4-Ethoxycarbonyl-2-n-heptyl-1-n-octyl-piperidin-3,6-dione

Ethyl 2-[N-(3'-ethoxycarbonylpropionyl)-N-octyl]-aminononanoate (5 g) was added dropwise to a suspension of sodium hydride (0.5 g) in refluxing tetrahydrofuran (200 ml). The mixture was refluxed under nitrogen overnight.

The reaction mixture was concentrated, water was added and the solution acidified with dilute hydrochloric acid. The product was extracted into ether and the ethereal solution was washed, dried over magnesium sulphate and evaporated in vacuo to give 4-ethoxycarbonyl-2-n-heptyl-1-n-octyl-piperidin-3,6-dione as a yellow oil (4.2 g).

Method Variant D

4-Ethoxycarbonyl-2-(6'-ethoxycarbonyl-n-hexyl)-1-(3''-benzyloxy-n-nonyl)-pyrrolidin-3,5-dione (m'=0; n=6; $R_1=C_2H_5$; $R_2=H$; $^1R_3=CH_2Ph$; $R_4=C_6H_{13}$)

A solution of diethyl 2-[N-(3'-benzyloxy-n-nonyl)-N-ethoxycarbonylacetyl]-aminoazelate (0.5 g) in hexamethylphosphoramide (5 ml) was added to a solution of potassium tert-butoxide (0.11 g) in hexamethylphosphoramide (5 ml). The mixture was stirred at room temperature for 1 hour.

The reaction mixture was poured into dilute hydrochloric acid and extracted with ether. The ether extracts were washed with brine and dried over anhydrous sodium sulphate to give a solution of 4-ethoxycarbonyl-2-(6'-ethoxycarbonyl-n-hexyl)-1-(3''-benzyloxy-n-nonyl)-pyrrolidin-3,5-dione.

The products shown in Table 5 were similarly prepared

TABLE 5

| Compound | m' | n | $R_1$ | $R_2$ | $'R_3$ | $R_4$ | Method Variant |
|---|---|---|---|---|---|---|---|
| 35 | 1 | 6 | $C_2H_5$ | H | $CH_2Ph$ | $C_6H_{13}$ | B |
| 36 | 0 | 6 | $C_2H_5$ | H | $CH_2Ph$ | $C_5H_{11}$ | B |
| 37 | 0 | 6 | $C_2H_5$ | H | $CH_2Ph$ | H | B |
| 38 | 1 | 6 | $C_2H_5$ | $CH_3$ | H | $C_5H_{11}$ | B |
| 39 | 1 | 6 | $C_2H_5$ | $CH_3$ | H | $C_6H_{13}$ | A |
| 40 | 1 | 6 | $C_2H_5$ | $CH_3$ | H | $C_7H_{15}$ | A |
| 41 | 1 | 6 | $C_2H_5$ | $CH_3$ | H | $C_8H_{17}$ | A |
| 42 | 1 | 7 | $C_2H_5$ | $CH_3$ | H | $C_6H_{13}$ | A |
| 43 | 1 | 6 | $C_2H_5$ | $CH_3$ | H | $CH(CH_3)C_5H_{11}$ | A |
| 44 | 0 | 6 | $C_2H_5$ | $CH_3$ | H | $C_4H_9$ | A |
| 45 | 0 | 6 | $C_2H_5$ | $CH_3$ | H | $C_5H_{11}$ | A |
| 46 | 0 | 6 | $C_2H_5$ | $CH_3$ | H | $C_7H_{15}$ | A |
| 47 | 0 | 6 | $C_2H_5$ | $CH_3$ | H | $C_8H_{17}$ | A |

TABLE 5-continued

| Compound | m' | n | R1 | R2 | 'R3 | R4 | Method Variant |
|---|---|---|---|---|---|---|---|
| 48 | 0 | 7 | C2H5 | CH3 | H | C6H13 | A |
| 49 | 0 | 5 | C2H5 | CH3 | H | C6H13 | A |
| 50 | 0 | 6 | C2H5 | C2H5 | H | C6H13 | A |
| 51 | 0 | 6 | CH3 | CH3 | H | C6H13 | A |

EXAMPLE 9

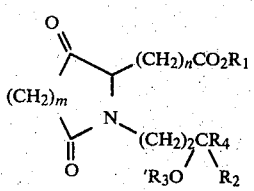

Method Variant A 2-(6'-Ethoxycarbonyl-n-hexyl)-1-(3"-hydroxy-3"-methyl-n-nonyl)pyrrolidin-3,5-dione (m=1; n=6; $R_1$=$C_2H_5$; $R_2$=$CH_3$; '$R_3$=H; $R_4$=$C_6H_{13}$)

A solution of 4-ethoxycarbonyl-2-(6'-ethoxycarbonyl-n-hexyl)-1-(3"-hydroxy-3"-methyl-n-nonyl)-pyrrolidin-3,5-dione in ether was allowed to stand over magnesium sulphate at room temperature overnight. The solution was filtered and the filtrate evaporated in vacuo to give 2-(6'-ethoxycarbonyl-n-hexyl)-1-(3"-hydroxy-3"-methyl-n-nonyl)-pyrrolidin-3,5-dione as a yellow oil.

Method Variant B 1-(3'-Benzyloxy-n-octyl)-2-(6"-ethoxycarbonyl-n-hexyl)-piperidin-3,6-dione (m=2; n=6; $R_1$=$C_2H_5$; $R_2$=H; '$R_3$=$CH_2Ph$; $R_4$=$C_5H_{11}$)

1-(3'-Benzyloxy-n-octyl)-4-ethoxycarbonyl-2-(6"-ethoxycarbonyl-n-hexyl)-piperidin-3,6-dione (8.3 g) was refluxed with lithium iodide dihydrate (4 g) in dry dimethylformamide (70 ml) for 3 hours. The solvent was evaporated in vacuo and the residue treated with very dilute hydrochloric acid. The product was extracted into ether and the ethereal solution was washed with water, dried over magnesium sulphate and evaporated in vacuo to give a pale yellow oil. The product was purified by column chromatography to give 1-(3'-benzyloxy-n-octyl)-2-(6"-ethoxycarbonyl-n-hexyl)-piperidin-3,6-dione as a pale yellow gum (2.0 g, 28% yield).

Method Variant C 1-(3'-Benzyloxy-n-octyl)-2-(6"-ethoxycarbonyl-n-hexyl)-pyrrolidin-3,5-dione (m=1; n=6; $R_1$=$C_2H_5$; $R_2$=H; '$R_3$=$CH_2Ph$, $R_4$=$C_5H_{11}$ A solution of 1-(3'-benzyloxy-n-octyl)-4-ethoxycarbonyl-2-(6"-ethoxycarbonyl-n-hexyl)-pyrrolidin-3,5-dione (5.4 g) in dry xylene was refluxed for 2 hours. The solvent was evaporated in vacuo and the product purified by gel filtration to give 1-(3'-benzyloxy-n-octyl)-2-(6"-ethoxycarbonyl-n-hexyl)-pyrrolidin-3,5-dione as a yellow gum (2.0 g, 43% yield).

The products shown in Table 6 were similarly prepared.

EXAMPLE 10

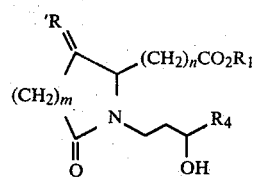

2-(6'-Ethoxycarbonyl-n-hexyl)-1-(3"-hydroxy-n-octyl)-piperidin-3,6-dione (m=2; n=6; 'R=0; $R_1$=$C_2H_5$; $R_4$=$C_5H_{11}$).

10% Palladium on charcoal (1.4 g) was added to a solution of 1-(3'-benzyloxy-n-octyl)-2-(6"-ethoxycarbonyl-n-hexyl)piperidin-3,6-dione (2.8 g) in dry dimethoxyethane (25 ml) and the mixture was hydrogenated at room temperature and atmospheric pressure for 1 hour. The reaction mixture was filtered through kieselguhr and the filtrate evaporated in vacuo to give 2-(6'-ethoxycarbonyl-n-hexyl)-1-(3"-hydroxy-n-octyl)-piperidin-3,6-dione (2.05 g) as a yellow gum.

The products shown in Table 7 were similarly prepared.

TABLE 6

| Compound | m | n | R1 | R2 | 'R3 | R4 | Method Variant |
|---|---|---|---|---|---|---|---|
| 52 | 2 | 6 | C2H5 | H | CH2Ph | C6H13 | B |
| 53 | 1 | 6 | C2H5 | H | CH2Ph | C6H13 | C |
| 54 | 1 | 6 | C2H5 | H | CH2Ph | H | C |
| 55 | 2 | 6 | C2H5 | CH3 | H | C5H11 | B |
| 56 | 2 | 6 | C2H5 | CH3 | H | C6H13 | B |
| 57 | 2 | 6 | C2H5 | CH3 | H | C7H15 | B |
| 58 | 2 | 6 | C2H5 | CH3 | H | C8H17 | B |
| 59 | 2 | 7 | C2H5 | CH3 | H | C6H13 | B |
| 60 | 2 | 6 | C2H5 | CH3 | H | CH(CH3)C5H11 | B |
| 61 | 1 | 6 | C2H5 | CH3 | H | C4H9 | A |
| 62 | 1 | 6 | C2H5 | CH3 | H | C5H11 | A |
| 63 | 1 | 6 | C2H5 | CH3 | H | C6H13 | A |
| 64 | 1 | 6 | C2H5 | CH3 | H | C7H15 | A |
| 65 | 1 | 6 | C2H5 | CH3 | H | C8H17 | A |
| 66 | 1 | 7 | C2H5 | CH3 | H | C6H13 | A |
| 67 | 1 | 5 | C2H5 | CH3 | H | C6H13 | A |
| 68 | 1 | 6 | C2H5 | C2H5 | H | C6H13 | A |
| 69 | 1 | 6 | CH3 | CH3 | H | C6H13 | A |
| 70 | 1 | 6 | n-C4H9 | CH3 | H | C6H13 | A |
| 71 | 1 | 6 | t-C4H9 | CH3 | H | C6H13 | A |

2-n-Heptyl-1-n-octyl-piperidin-3,6-dione was similarly prepared using Method Variant C.

TABLE 7

| Compound | m | n | 'R | R1 | R4 |
|---|---|---|---|---|---|
| 72 | 2 | 6 | H,OH | C2H5 | H |
| 73 | 2 | 6 | 0 | C2H5 | C5H11 |
| 74 | 2 | 6 | 0 | C2H5 | H |
| 75 | 1 | 6 | 0 | C2H5 | C5H11 |
| 76 | 1 | 6 | H,OH | C2H5 | C5H11 |
| 77 | 1 | 6 | 0 | C2H5 | C6H13 |
| 78 | 2 | 6 | 0 | C2H5 | C6H13 |

4-Ethoxycarbonyl-2-(6'-ethoxycarbonyl-n-hexyl)-1-(3"-hydroxy-propyl)-piperidin-3,6-dione was similarly prepared.

EXAMPLE 11

2-(6'-Ethoxycarbonyl-n-hexyl)-3-hydroxy-1-(3''-hydroxy-n-octyl)pyrrolidin-5-one Sodium borohydride (100 mg) was added in portions to a stirred solution of 2-(6'-ethoxycarbonyl-n-hexyl)-1-(3''-hydroxy-n-octyl)-pyrrolidin-3,5-dione (870 mg) in dry ethanol (10 ml). Stirring was continued for 2 hours at room temperature.

The solvent was evaporated in vacuo and the residue was dissolved in ether. The ethereal solution was washed with very little dilute hydrochloric acid and with water, dried over magnesium sulphate and evaporated in vacuo to give a yellow gum. The product was purified by chromatography to give 2-(6'-ethoxycarbonyl-n-hexyl)-3-hydroxy-1-(3''-hydroxy-n-octyl)-pyrrolidin5-one as a colourless gum (410 mg, 47% yield).

The products shown in Table 8 were similarly prepared:

TABLE 8

$$\text{structure with } (CH_2)_m, (CH_2)_nCO_2R_1, N, (CH_2)_2CR_4, 'R_3O, R_2, O$$

| Compound | m | n | $R_1$ | $R_2$ | $'R_3$ | $R_4$ |
|---|---|---|---|---|---|---|
| 79 | 2 | 6 | $C_2H_5$ | H | $CH_2Ph$ | $C_5H_{11}$ |
| 80 | 2 | 6 | $C_2H_5$ | H | $CH_2Ph$ | H |
| 81 | 1 | 6 | $C_2H_5$ | H | $CH_2Ph$ | $C_5H_{11}$ |
| 82 | 1 | 6 | $C_2H_5$ | H | $CH_2Ph$ | H |
| 83 | 1 | 6 | $C_2H_5$ | H | $CH_2Ph$ | $C_6H_{13}$ |
| 84 | 1 | 6 | $C_2H_5$ | $CH_3$ | H | $C_5H_{11}$ |
| 85 | 2 | 6 | $C_2H_5$ | $CH_3$ | H | $C_6H_{13}$ |
| 86 | 1 | 6 | $C_2H_5$ | $CH_3$ | H | $C_6H_{13}$ |
| 87 | 2 | 6 | $C_2H_5$ | $CH_3$ | H | $CH(CH_3)C_5H_{11}$ |
| 88 | 2 | 6 | $C_2H_5$ | $CH_3$ | H | $C_7H_{15}$ |
| 89 | 1 | 6 | $C_2H_5$ | $CH_3$ | H | $C_7H_{15}$ |
| 90 | 2 | 6 | $C_2H_5$ | $CH_3$ | H | $C_8H_{17}$ |
| 91 | 1 | 6 | $C_2H_5$ | $C_2H_5$ | H | $C_6H_{13}$ |
| 92 | 1 | 6 | $C_2H_5$ | $CH_3$ | H | $C_4H_9$ |
| 93 | 1 | 7 | $C_2H_5$ | $CH_3$ | H | $C_6H_{13}$ |
| 94 | 1 | 5 | $C_2H_5$ | $CH_3$ | H | $C_6H_{13}$ |
| 95 | 1 | 6 | $C_2H_5$ | $CH_3$ | H | $C_8H_{17}$ |
| 96 | 2 | 6 | $C_2H_5$ | H | H | $C_5H_{11}$ |
| 97 | 2 | 6 | $C_2H_5$ | H | H | $C_6H_{13}$ |
| 98 | 1 | 6 | $C_2H_5$ | H | H | $C_6H_{13}$ |

Compound 99, 2-n-Heptyl-3-hydroxy-1-n-octyl-piperidin-6-one, and 2-(6'-ethoxycarbonyl-n-hexyl)-3-hydroxy-1-n-octylpiperidin-6-one were also prepared similarly.

EXAMPLE 12

2-(6'-Carboxy-n-hexyl)-3-hydroxy-1-(3''-hydroxy-3''-methyl-n-decyl)-pyrrolidin-5-one A 10% solution of potassium carbonate (20 ml) was added to a solution of 2-(6'-ethoxycarbonyl-n-hexyl)-3-hydroxy-1-(3''-hydroxy-3''-methyl-n-decyl)-pyrrolidin-5-one (2 g) in ethanol (20 ml). This mixture was gently refluxed for 2 hours.

The solvent was evaporated in vacuo and the residue was taken up in water. The aqueous solution was extracted with ether and acidified with dilute hydrochloric acid. The acid solution was extracted with ether and this ethereal solution was washed with water, dried over magnesium sulphate and evaporated in vacuo to give a colourless oil. The product was purified by chromatography to give 2-(6'-carboxy-n-hexyl)-3-hydroxy-1-(3''-hydroxy-3''-methyl-n-decyl)-pyrrolidin-5-one as a colourless oil (900 mg, 48% yield).

EXAMPLE 13

2-(6'-Carboxy-n-hexyl)-1-(3''-hydroxy-n-nonyl)-pyrrolidin-3,5-dione

A solution of 2-(6'-ethoxycarbonyl-n-hexyl)-1-(3''-hydroxyn-nonyl)-pyrrolidin-3,5-dione (2 g) in ethanol (25 ml) was added dropwise to a solution of 10% sodium hydroxide (25 ml) in ethanol (25 ml). The mixture was refluxed for 3 hours.

The solvent was evaporated in vacuo and the residue was dissolved in water. The aqueous solution was extracted with ether. acidified and the acid solution extracted twice with ether. These ether extracts were combined, washed with saturated brine, dried over magnesium sulphate and evaporated in vacuo to give 2-(6'-carboxy-n-hexyl)-1-(3''-hydroxy-n-nonyl)-pyrrolidin-3,5-dione as a colourless oil (1.5 g, 80% yield).

EXAMPLE 14

1-(3'-Benzyloxy-n-octyl)-3-hydroxy-2-(7''-hydroxy-n-heptyl)piperidine 1-(3'-Benzyloxy-n-octyl)-2-(6''-ethoxycarbonyl-n-hexyl)piperidin-3,6-dione (1 g) was stirred, under reflux, with lithium aluminium hydride (156 mg) in dry ether (30 ml) for 4 hours. The mixture was cooled in an ice-bath and water (1.5 ml) was added dropwise. The reaction mixture was stirred at room temperature for 30 minutes and filtered. The residue was washed several times with ether and the combined ether solutions were dried over magnesium sulphate and evaporated in vacuo to give 1-(3'-benzyloxy-n-octyl)-3-hydroxy-2-(7''-hydroxy-n-heptyl)piperidine as a yellow oil (730 mg, 82% yield).

The products shown in Table 9 were similarly prepared.

TABLE 9

$$\text{structure with } (CH_2)_m, (CH_2)_nCH_2OH, OH, N, (CH_2)_2CR_4, 'R_3O, R_2$$

| Compound | m | n | $R_2$ | $'R_3$ | $R_4$ |
|---|---|---|---|---|---|
| 100 | 2 | 6 | H | H | $C_5H_{11}$ |
| 101 | 1 | 6 | H | $CH_2Ph$ | $C_5H_{11}$ |
| 102 | 1 | 6 | H | H | $C_5H_{11}$ |
| 103 | 2 | 6 | H | $CH_2Ph$ | H |
| 104 | 2 | 6 | H | $CH_2Ph$ | $C_5H_{11}$ |
| 105[a] | 2 | 6 | H | H | $C_6H_{13}$ |
| 106 | 1 | 6 | H | $CH_2Ph$ | H |
| 107[a] | 1 | 6 | H | $CH_2Ph$ | $C_6H_{13}$ |
| 108[a] | 1 | 6 | H | H | $C_6H_{13}$ |
| 109[a] | 2 | 6 | $CH_3$ | H | $C_6H_{13}$ |
| 110[a] | 1 | 6 | $CH_3$ | H | $C_7H_{15}$ |
| 111[a] | 2 | 6 | $CH_3$ | H | $C_8H_{17}$ |

[a] Product purified by chromatography

Compound 112, 2-n-heptyl-3-hydroxy-1-n-octyl-piperidine was also prepared similarly.

EXAMPLE 15

2-(6'-Ethoxycarbonyl-n-hexyl)-1-(3"-oxo-n-octyl)-piperidin-3,6-dione

Jones' reagent was added dropwise to a solution of 2-(6'-ethoxycarbonyl-n-hexyl)-1-(3"-hydroxy-n-octyl)-piperidine-3,6-dione (500 mg) in acetone (10 ml) at 0° until the yellow colour persisted. The stirred solution was allowed to warm to room temperature and ether (50 ml) and water (50 ml) were added. The organic phase was separated, washed with water, dried over magnesium sulphate and evaporated in vacuo to give (-2(6'-ethoxycarbonyl-n-hexyl)-1-(3"-oxo-n-octyl)-piperidine-3,6-dione as a yellow gum (500 mg, quantitive yield).

EXAMPLE 16

3-Benzyloxy-2-n-heptyl-1-n-octyl-piperidine

A solution of 2-n-heptyl-3-hydroxy-1-n-octyl-piperidine (2.8 g) in dry dioxan (20 ml) was added dropwise to a stirred suspension of sodium hydride (216 mg) in dry dioxan (5 ml) and the mixture was refluxed for 1 hour. Benzyl bromide (1.54 g) in dry dioxan (5 ml) was added dropwise to the cooled solution and the mixture was refluxed overnight.

The solvent was evaporated in vacuo and the residue was partitioned between ether and water. The ether phase was washed with water, dried over magnesium sulphate and evaporated in vacuo. The product was purified by column chromatography to give 3-benzyloxy-2-n-heptyl-1-n-octyl-piperidine as a yellow oil (1.3 g, 36% yield).

EXAMPLE 17

2-n-Heptyl-1-n-octyl-piperidin-3-one

Jones' reagent (116.1 ml) was added dropwise to a stirred solution of 2-n-heptyl-3-hydroxy-1-n-octyl-piperidine (16.6 g) in acetone (160 ml) at room temperature. The reaction mixture was stirred for 6 hours and filtered through kieselguhr. The residue was washed several times with ether and the combined organic solutions were extracted with 5% sodium hydroxide solution. The aqueous phase was washed with ether and the combined organic phases were washed with water, dried over magnesium sulphate and evaporated in vacuo. The product was purified by chromatography to give 2-n-heptyl-1-n-octyl-piperidin-3-one as a yellow gum (5.71 g, 34% yield).

EXAMPLE 18

2-n-Heptyl-3-hydroxy-3-methyl-1-n-octyl-piperidine

Methyl lithium (7 ml, 2 M solution in ether) was injected, under nitrogen, into a stirred solution of 2-n-heptyl-1-n-octylpiperidin-3-one (3.4 g) in dry ether (100 ml) at −78°. The mixture was allowed to warm gradually to room temperature. After 3 hours, thin layer chromatography indicated that some starting material remained. The solution was cooled to −78° and methyl lithium (3 ml, 2 M solution in ether) was injected. The mixture was allowed to warm gradually to room temperature and was allowed to stand for 2 days. Water (10 ml) was added dropwise and the ether phase was separated, dried over magnesium sulphate and evaporated in vacuo. The product was purified by column chromatography to give 2-n-heptyl-3-hydroxy-3-methyl-1-n-octylpiperidine as a yellow gum (1.47 g, 41% yield).

EXAMPLE 19

2-n-Heptyl-3-hydroxy-1-n-octyl-piperidine hydrogen tartrate 2-n-Heptyl-3-hydroxy-1-n-octyl-piperidine (550 mg) and D-tartaric acid (241 mg) were mixed together in acetone. The solvent was evaporated in vacuo to give 2-n-heptyl-3-hydroxy1-n-octyl-piperidine hydrogen tartrate as a yellow gum (740 mg, quantitive yield).

EXAMPLE 20

3-Acetoxy-2-(7'-acetoxy-n-heptyl)-1-(3"-benzyloxy-n-octyl)piperidine 1-(3'-Benzyloxy-n-octyl)-3-hydroxy-2-(7"-hydroxy-n-heptyl)piperidine (2 g) in dry benzene (30 ml) was treated with acetic anhydride (1.2 ml). The mixture was stirred overnight at room temperature.

The solvent was evaporated in vacuo and the residue was dissolved in ether (300 ml). The ethereal solution was washed with concentrated sodium hydroxide solution and with brine, dried over magnesium sulphate and evaporated in vacuo. The product was purified by column chromatography to give 3-acetoxy2-(7'-acetoxy-n-heptyl)-1-(3"-benzyloxy-n-octyl)-piperidine as a yellow oil (1.05 g, 43% yield).

EXAMPLE 21

3-Dioxolan-2-n-heptyl-1-n-octyl-piperidin-6-one

Ethylene glycol (1.2 g) and toluene p-sulfonic acid (30 mg) were added to a solution of 2-n-heptyl-1-n-octyl-piperidin-3,6-dione (0.6 g) in dry tolune (25 ml) and the mixture was refluxed under a Dean and Stark head for 3 hours.

The reaction mixture was diluted with water and extracted with ether. The ethereal solution was washed with sodium carbonate solution and with water, dried over magnesium sulphate and evaporated in vacuo to give 3-dioxolan-2-n-heptyl-1-n-octylpiperidin-6-one as a yellow oil (576 mg. 85% yield).

EXAMPLE 22

2-(6'-Ethoxycarbonyl-n-hexyl)-1-(3"-hydroxy-3"-methyl-n-decyl)piperidin-6-one-3-semicarbazone 2-(6'-Ethoxycarbonyl-n-hexyl)-1-(3"-hydroxy-3"-methyl-n-decyl)-piperidin-3,6-dione (750 mg) was added to a solution of semicarbazide hydrochloride (1 g) and sodium acetate (1.5 g) in water (10 ml). Ethanol was added until a clear solution was obtained and the mixture was shaken for 1 hour.

The reaction mixture was extracted with ether and the ethereal solution was washed with brine, dried over magnesium sulphate and evaporated in vacuo. The product was purified by preparative layer chromatography and crystallized from ether to give 2-(6'-ethoxycarbonyl-n-hexyl)-1-(3"hydroxy-3"-methyl-n-decyl)-piperidin-6-one-3-semicarbazone as a white solid (260 mg. 31% yield), m.p. 88°.

EXAMPLE 23

Pharmacological Data

The compounds were tested for prostaglandin-like and for prostaglandin antagonist activity in a number of pharmacological tests.

1. Anti-secretory/anti-ulcer activity a. The compounds were examined for their ability to inhibit pentagastrin-stimulated gastric acid secretion in the anaesthetised, perfused rat stomach preparation (Ghosh and Schild preparation).

M. N. Ghosh and H. O. Schild, (1958), Brit. J. Pharmacol, 13, 54.

The compounds were given intravenously. Some of the results are shown in Table 10.

TABLE 10

| Compound Number | Active dose range mg/kg | ED$_{50}$ mg/kg |
|---|---|---|
| 56 | 0.5 → 20 | — |
| 60 | 0.5 → 5 | 1.0 |
| 62 | 0.1 → 5 | 0.72 |
| 63 | 0.05 → 0.5 | 0.09 |
| 77 | 1 → 10 | 2.6 |
| 78 | 1 → 10 | — | b. The compounds were examined for their ability to inhibit gastric acid secretion in the pyloric ligated rat model (Shay rat preparation).

H. Shay, S. A. Komarov, S. S. Fels, D. Merance, M. Gruenstein and H. Siplet, (1945), Gastroenerology, 5, 43.

When given subcutaneously twice in a 3 hour Shay rat preparation, once at the time of ligation and again 1.5 hours after ligation, Compound 63 lowered the total titratable acidity in the stomach by inhibiting the volume of secretion and by decreasing the H$^+$ concentration. The ED$_{50}$ was 2.25 mg/kg×2, s.c.

When given subcutaneously once in a 3 hour Shay rat preparation at the time of ligation, Compound 63 had an ED$_{50}$ of 5.3 mg/kg, s.c. Similarly, Compound 63 was active when given intraduodenally in the Shay rat preparation.

c. The compounds were examined for their ability to inhibit gastric acid secretion, stimulated by pentagastrin infusion, in the chronic fistula rat preparation.

P. H. Guth and R. Mendick, (1965), Amer. J. Gastroenterology, 44, 545.

Compound 63 when given subcutaneously was very effective in inhibiting acid secretion at 2-5 mg/kg, s.c.

d. Anti-ulcer activity was determined in a 5 hour indomethacin-induced (50 mg/kg, i.p.) ulcer test in fasted rats. Compound 63 inhibited ulceration by 71% when given at 20 mg/kg, s.c., twice during the course of the test.

2. Respiratory system
Bronchodilator activity a. The compounds were examined for their ability to inhibit 5-hydroxy-tryptamine-induced bronchoconstriction in the anaesthetised, artifically respired guinea pig (Konsett-Rossler preparation).

H. Konsett and R. Rossler, (1940), Naunyn-Schneidebergs Arch. Exp. Path. Pharmak., 195, 71.

After preparation of the guinea pig, a dose of 5-hydroxytryptamine producing an adequate response was determined by dosing, i.v., every 6 minutes. This dose was usually 10 μg. After a standard response was obtained, compounds were given intra-venously 2 minutes prior to the next standard dose and dosing of 5-hydroxytryptamine was continued every 6 minutes until the response returned to control values. Some of the results are shown in Table 11.

TABLE 11

| Compound Number | ED$_{50}$ μg/kg |
|---|---|
| 57 | 253 |
| 62 | 88 |
| 63 | 8 |
| 64 | 11 |
| 77 | 380 |

TABLE 11-continued

| Compound Number | ED$_{50}$ μg/kg |
|---|---|
| 86 | 505 | b. The compounds were examined for their ability to protect against aerosol administered, histamine-induced asphyxic collapse in guinea pigs.

M. A. Wasserman and R. L. Griffen, (1975), Am. Rev. Resp. Dis., 111, 946.

Many of the compounds, such as Compounds 63 and 64, were very effective in protecting against histamine challenge.

3. Cardiovascular activity a. The effect of the compounds on arterial blood pressure was determined in the anaesthetised, normotensive rat. The rat preparation was similar to that desribed in "Pharmacological experiments on intact preparations", E. and S. Livingstone, Edinburgh and London, 1970, p. 63.

The compounds were administered intravenously and some of the results are shown in Table 12. The active compounds were predominantly depressor agents in the normotensive rat.

TABLE 12

| Compound number | Dose range mg/kg | % Depression at 1 mg/kg |
|---|---|---|
| 62 | 0.001 → 1.0 | 70 |
| 63 | 0.001 → 1.0 | 60 |
| 77 | 0.001 → 1.0 | 30 |
| 78 | 0.001 → 1.0 | 30 |
| 105 | 0.001 → 1.0 | 20 | b. The vasodilator activity of the compounds was determined in the femoral artery of the hind limb of the anaesthetised beagle dog. The method used was similar to that described by J. Nakano and J. R. McCurdy, (1967), J. Pharmac. Exp. Ther., 156, 538.

The compounds were administered into the iliac artery and the effects on both flow and pressure in the hind limb were recorded. Changes in vascular resistance (R) were calculated from the following expression:

$$R = \frac{\text{mean arterial pressure}}{\text{mean flow}}$$

Some of the compounds, for example Compounds 63, 73 and 112, decreased vascular resistance over a dose range of 0.01-1 mg/kg, when given intra-arterially.

In other experiments the compounds were administered into the left femoral vein and the right femoral arterial pressure and cardiac output were monitored. From these experiments, total peripheral resistance (TPR) was calculated from the expression:

$$TPR = \frac{\text{mean arterial pressure}}{\text{cardiac output}}$$

Some of the compounds, such as Compounds 63, 73 and 112, decreased total peripheral resistance over a dose range of 0.01-10 mg/kg, when given intravenously.

c. The anti-hypertensive activity of the compounds was determined in the renal hypertensive rat. Rats were made hypertensive by nephrectomy and treatment with deoxycorticosterone acetate/NaCl. The compounds were administered orally to a group of 3 hypertensive rats at a dose level of 100 mg/kg and their blood pressure was monitored after 4, 6 and 24 hours.

Compound 73 gave a 16% fall in blood pressure after 4 hours. The blood pressure had risen to normal hypertensive levels after 6 hours.

4. Inhibition of platelet aggregation a. The compounds were examined for their ability to inhibit guinea pig platelet aggregation induced, in vitro, by $5.45 \times 10^{-7}$ M adenosine diphosphate (ADP).

The method consisted of diluting the compound immediately before use from a 10 mg/ml solution in ethanol to a 1 mg/ml solution with saline and then adding the appropriate volume to 0.5 ml of platelet rich plasma. The mixture was stirred at 37° C. for 1 minute before 25 μl of an ADP solution was added to give a final ADP concentration of $5.45 \times 10^{-7}$ M. The aggregation response was then recorded relative to the control.

Some of the results are shown in Table 13.

TABLE 13

| Compound number | $IC_{50}$ μM |
|---|---|
| 56 | 51 |
| 60 | 11 |
| 62 | 20 |
| 63 | 1.3 |
| 64 | 9.0 |
| 68 | 4.0 |
| 73 | 44 |
| 76 | 147 |
| 77 | 5.4 |
| 86 | 55 | b. The compounds were examined for their ability to inhibit human platelet aggregation induced, in vitro, either by adenosine diphosphate (ADP) or collagen. The compounds were added in saline or dimethylformamide to platelet rich plasma at 37° C. to give a final concentration of $10^{-4}$ M. After 3 minutes the platelets were challenged with ADP or collagen. The aggregation response was then recorded relative to the control. Some of the results are shown in Table 14. Only compounds giving a greater than 50% inhibition at $10^{-4}$ M were regarded as active.

TABLE 14

| Compound number | % Inhibition at $10^{-4}$ M | |
|---|---|---|
| | ADP | Collagen |
| 73 | 87 | 100 |
| 75 | — | 61 |
| 76 | — | 79 |
| 78 | — | 65 |
| 102 | — | 71 |
| 105 | — | 78 |
| 112 | — | 77 |

The $IC_{50}$ for Compound 73 against collagen-induced aggregration was 2.8 μM.

5. Smooth muscle activity a. Gerbil colon in vitro

The compounds were tested for prostaglandin-like and for prostaglandin antagonist activity on the isolated perfused gerbil colon preparation (smooth muscle). This has been shown by J. R. Weeks, J. R. Schultz and W. E. Brown, (1968), J. App. Physiol, 25, 783, to have greater precision and sensitivity than other preparations. A 15 mm portion of the descending colon is suspended in an organ bath and perfused with De Jalon's saline at 32° C. Compounds were given in a three minute cycle with a 45 second contact time and a 15 second washout time. Antagonist compounds were given with a one minute pre-contact time.

Prostaglandin-like activity was determined using the method of H. O. Schlid, (1942), J. Physiol., 101, 115, which is a standard 4×4 latin square assay. Some of the compounds stimulated the gerbil colon to contract which is a prostaglandin-like effect, and the results are shown in Table 15.

TABLE 15

| Compound number | Concentration/ml. for contractions (μg/ml) |
|---|---|
| 74 | 4–8 |
| 75 | 0.2–0.5 |
| 100 | 0.01–0.02 |
| 101 | 0.04–0.10 |
| 102 | 0.04–0.10 |

Antagonist activity was determined by measuring the percentage reduction of the contraction to two standard doses of prostaglandin $F_{2\alpha}$ which gave responses between 20% and 80% of maximum response. From this data the $IC_{50}$ values were calculated and the results for some of the compounds are shown in Table 16.

TABLE 16

| Compound number | $IC_{50}$ μg/ml |
|---|---|
| 73 | 3.4 |
| 79 | 0.76 |
| 80 | 3.1 |
| 81 | 0.17 |
| 98 | 2.15 |
| 99 | 1.55 |
| 103 | 0.35 |
| 104 | 0.11 | b. Rat stomach strip in vitro

Some of the compounds were tested for prostaglandin-like activity on the isolated rat stomach strip preparation. Some of the compounds weakly stimulated the isolated tissue.

6. Antifertility activity

Antifertility activity was determined by subcutaneous dosing of female mice for 5 days pre-coitally and 10 days post-coitally. Three female mice per group were used and these were mated with males of proven fertility and mating confirmed by examination for copulation plugs.

Some of the compounds, such as Compounds 108 and 112, were active at 50–100 mg/kg, s.c.

The pharmacological and therapeutic values of compounds with prostaglandin-like activity, for example, as anti-hypertensive agents, as fertility control agents, as inhibitors of gastric secretion and as bronchodilators is well known. S. Bergstrom, L. A. Carlson and J. R. Weeks, (1968), Pharm. Rev., 20, 1; F. Cassidy, (1971), Rep. Prog. Appl. Chem., 56,695; The Prostaglandins, Progress in Research, S. M. M. Karim, Medical and Technical Publishing Co. Ltd., Oxford and Lancaster, 1972.

Compounds which antagonise the action of prostaglandins are of pharmacological significance. Such prostaglandin antagonists are of potential value in the control of gastro-intestinal hypermotility, in the prevention of premature labour and in the control of inflammation. (see The Prostaglandins, loc. cit.).

We claim:

1. A compound of the formula:

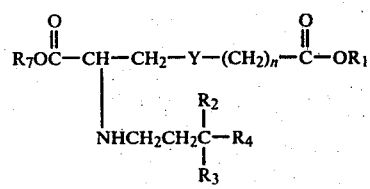

wherein
each of $R_1$ and $R_7$ is the residue of an alcohol of the formula $R_1OH$ or $R_7OH$ containing 1 to 12 carbon atoms;
$R_2$ is hydrogen or alkyl of 1 to 4 carbon atoms;
$R_3$ is hydroxy, acyloxy of 1 to 4 carbon atoms or benzyloxy;
$R_4$ is hydrogen or alkyl of 1 to 9 carbon atoms;
Y is ethylene or vinylene and
n has a value of from 1 to 8.

2. A compound according to claim 1 wherein Y is ethylene and n has a value of 5, 6 or 7.

3. A compound according to claim 2 wherein n has a value of 6.

4. A compound according to claim 2 wherein $R_2$ is hydrogen, methyl or ethyl.

5. A compound according to claim 4 wherein $R_3$ is hydroxy or benzyloxy.

6. A compound according to claim 4 wherein $R_4$ is butyl, pentyl, hexyl, heptyl or hept-2-yl.

7. A compound according to claim 6 wherein each of $R_1$ and $R_2$ is methyl or ethyl.

8. A compound according to claim 1 and selected from the group consisting of the dimethyl and diethyl esters of 2-(3-benzyloxynonylamino)azelaic acid; 2-(3-benzyloxyoctylamino) azelaic acid; 2-(3-benzyloxypropylamino)azelaic acid; 2(-3-hydroxy-3-methylheptylamino)azelaic acid; 2-(3-hydroxy-3-methyloctylamino)azelaic acid; 2-(3-hydroxy-3-methylnonylamino)azelaic acid; 2-(3-hydroxy-3-methyldecylamino)azelaic acid; 2-(3-hydroxy-3-methylundecylamino)azelaic acid; 2-(3-hydroxy-3-ethylnonylamino)azelaic acid; 2-(3-hydroxy-3-methylnonylamino)suberic acid; 2-(3-hydroxy-3-methylnonylamino)sebacic acid and 2-(3-hydroxy-3,4-dimethylnonylamino)azelaic acid.

* * * * *